(12) United States Patent
Sakurai

(10) Patent No.: US 10,485,464 B2
(45) Date of Patent: Nov. 26, 2019

(54) SPECTROMETRIC APPARATUS AND STORAGE CASE

(71) Applicant: Seiko Epson Corporation, Tokyo (JP)

(72) Inventor: Kazunori Sakurai, Chino (JP)

(73) Assignee: Seiko Epson Corporation (JP)

( * ) Notice: Subject to any disclaimer, the term of this patent is extended or adjusted under 35 U.S.C. 154(b) by 1038 days.

(21) Appl. No.: 14/926,174

(22) Filed: Oct. 29, 2015

(65) Prior Publication Data

US 2016/0120450 A1 May 5, 2016

(30) Foreign Application Priority Data

Oct. 30, 2014 (JP) .................................. 2014-221149

(51) Int. Cl.
| | | |
|---|---|---|
| *A61B 5/1455* | (2006.01) | |
| *G01J 3/02* | (2006.01) | |
| *A61B 5/00* | (2006.01) | |
| *G01J 3/26* | (2006.01) | |
| *G01N 21/01* | (2006.01) | |
| *G01N 21/31* | (2006.01) | |

(52) U.S. Cl.
CPC ........ *A61B 5/14552* (2013.01); *A61B 5/6833* (2013.01); *G01J 3/0202* (2013.01); *G01J 3/0205* (2013.01); *G01J 3/0259* (2013.01); *G01J 3/0291* (2013.01); *G01J 3/26* (2013.01); *G01N 21/01* (2013.01); *G01N 21/31* (2013.01); *A61B 5/6831* (2013.01); *A61B 2560/0406* (2013.01); *A61B 2562/0233* (2013.01); *A61B 2562/185* (2013.01); *G01N 2201/0227* (2013.01); *G01N 2201/064* (2013.01)

(58) Field of Classification Search
CPC .. A61B 5/1455; A61B 5/14551; A61B 5/6833
See application file for complete search history.

(56) References Cited

U.S. PATENT DOCUMENTS

| 5,697,367 A | 12/1997 | Lewis et al. |
|---|---|---|
| 5,795,292 A | 8/1998 | Lewis et al. |
| | (Continued) | |

FOREIGN PATENT DOCUMENTS

| EP | 0 756 847 A1 | 2/1997 |
|---|---|---|
| JP | H09-117439 A | 5/1997 |
| | (Continued) | |

*Primary Examiner* — Eric F Winakur
(74) *Attorney, Agent, or Firm* — Harness, Dickey & Pierce, P.L.C.

(57) ABSTRACT

A biological body inspection apparatus includes a measurement module that acquires an amount of light having a wavelength under measurement contained in light incident on the measurement module and an enclosure that accommodates the measurement module and has a window that transmits light traveling toward the measurement module. An adhesive member is provided on a surface of the enclosure at least in an area thereof that surrounds the window. The adhesive member has a light blocking section that is located in an area outside the window and surrounds the window in a plan view in the direction along the optical axis of the light traveling toward the measurement module and blocks light that belongs to a measurement wavelength region within which at least the wavelength under measurement is present.

7 Claims, 9 Drawing Sheets

(56) References Cited

U.S. PATENT DOCUMENTS

| | | | |
|---|---|---|---|
| 9,138,181 B2 * | 9/2015 | Haisley | A61B 5/1455 |
| 2005/0075553 A1 | 4/2005 | Sakai et al. | |
| 2012/0206731 A1 | 8/2012 | Sano et al. | |
| 2013/0060098 A1 | 3/2013 | Thomsen et al. | |
| 2014/0340686 A1 | 11/2014 | Sano et al. | |
| 2015/0282762 A1 | 10/2015 | Lechot et al. | |
| 2016/0085065 A1 | 3/2016 | Sano et al. | |

FOREIGN PATENT DOCUMENTS

| | | |
|---|---|---|
| JP | 2005-160641 A | 6/2005 |
| JP | 4201683 B2 | 12/2008 |
| JP | 2010-175758 A | 8/2010 |
| JP | 2012-168438 A | 9/2012 |
| JP | 2013-515528 A | 5/2013 |
| JP | 2014-052594 A | 3/2014 |
| WO | WO-2014-072231 A | 5/2014 |

* cited by examiner

SPECTROMETRIC APPARATUS AND STORAGE CASE

BACKGROUND

1. Technical Field

The present invention relates to a spectrometric apparatus and a storage case.

2. Related Art

There is a known apparatus that irradiates a subject with light and receives light from the subject in the form of light of a predetermined wavelength to acquire the amount of light of the predetermined wavelength (JP-A-2005-160641, for example).

JP-A-2005-160641 describes a pulse detection apparatus that causes a light emitter including an infrared LED (light emitting diode) and a green LED to emit light, receives light from a subject with a photodiode (light reception section), and detects the pulse of the subject based on a result of the light reception.

In the pulse detection apparatus, the photodiode is disposed in an enclosure, and the light is introduced into the enclosure through an opening provided in the enclosure. A protrusion is so formed that it surrounds the opening provided in the enclosure. The pulse measurement is performed with the protrusion being in contact with the subject.

To use the apparatus described in JP-A-2005-160641, however, the apparatus is pressed against the subject to allow the protrusion to deform the subject so that external light does not enter the enclosure through a gap between the enclosure and the subject. It is therefore necessary to keep pressing the apparatus, and the gap may be created when a pressing force changes. If the gap is created, external light enters the enclosure, and measurement accuracy therefore undesirably lowers.

SUMMARY

An advantage of some aspects of the invention is to provide a spectrometric apparatus and a storage case that prevent external light from entering to improve measurement accuracy.

A spectrometric apparatus according to an application example of the invention includes a measurement module that acquires an amount of light having a wavelength under measurement contained in light incident on the measurement module and an enclosure that accommodates the measurement module and has a window that transmits light traveling toward the measurement module. An adhesive member is provided on a surface of the enclosure at least in an area thereof that surrounds the window, and the adhesive member has a light blocking section that is located in an area outside the window and surrounds the window in a plan view in a direction along an optical axis of the light traveling toward the measurement module and blocks light that belongs to a measurement wavelength region within which at least the wavelength under measurement is present.

In the spectrometric apparatus according to the application example, the adhesive member is disposed on the surface of the enclosure at least in an area including the window. The adhesive member has the light blocking section, which is located in an area outside the window in the plan view in the direction along the optical axis of the light received with the measurement module and blocks at least light that belongs to a measurement wavelength region.

In the application example, when the spectrometric apparatus is pressed against a subject under measurement with the side where the window is provided facing the subject under measurement, the enclosure is allowed to come into intimate contact with the subject via the adhesive member. The light blocking section of the adhesive member that is in intimate contact with the subject can therefore block external light. Therefore, a situation in which external light having passed through a gap between the subject and the enclosure and further through the window and including light belonging to the measurement wavelength region reaches the interior of the enclosure and is received with the measurement module can be avoided, whereby measurement accuracy can be improved.

In the spectrometric apparatus according to the application example, it is preferable that the light blocking section is provided in an area inside an outer circumferential edge of the adhesive member in the plan view.

In the application example with this configuration, a light transmissive section is provided in an area outside the light blocking section, that is, the light blocking section is provided in an area inside the outer circumferential edge of the adhesive member. The adhesive member tends to peel off at the outer circumferential edge thereof. If the light blocking section is provided along the outer circumferential edge, there is a risk of entry of external light through a portion where the light blocking section peels off. In contrast, in the application example, in which the light blocking section is provided in the area inside the outer circumferential edge of the adhesive member where it tends to peel off, a situation in which the light blocking section peels off can be avoided, whereby entry of external light can be more reliably avoided.

In the spectrometric apparatus according to the application example, it is preferable that the light blocking section is provided along an outer edge of the window in the plan view.

In the application example with this configuration, the light blocking section is provided along the outer edge of the window. In the configuration described above, since the light blocking section is provided along the window, the entry of external light described above can be more effectively avoided.

In the spectrometric apparatus according to the application example, it is preferable that the adhesive member has a light transmissive section that transmits at least the light that belongs to the measurement wavelength region, and that the light blocking section and the light transmissive section are formed integrally with each other.

In the application example with this configuration, since the adhesive member is formed of the light blocking section and the light transmissive section integrated with each other, for example, the adhesive member can be exchanged through detachment thereof as a whole. Further, to place the adhesive member on the enclosure, the adhesive member can be disposed as a whole. The light blocking section can therefore be disposed in an appropriate position through alignment of the adhesive member with the enclosure. The adhesive member can thus be readily exchanged.

In the spectrometric apparatus according to the application example, it is preferable that the adhesive member has a light transmissive section that is provided in a position where the light transmissive section overlaps with the window in the plan view and transmits at least the light that belongs to the measurement wavelength region, that the window has an opening provided in the enclosure and a light transmissive member disposed in the opening, and that the light transmissive section has a refractive index that differs from a refractive index of the light transmissive member by an amount smaller than or equal to a predetermined threshold.

In the application example, the adhesive member has a light transmissive section that is provided in a position where the light transmissive section overlaps with the window and transmits the light that belongs to the measurement wavelength region, and the light transmissive section has a refractive index that differs from a refractive index of the light transmissive member by an amount smaller than or equal to a predetermined threshold. In the configuration described above, the difference in refractive index at the interface with the light transmissive member can be smaller than the difference in a case where an air layer is formed between the subject and the window. Reflection at the interface can therefore be suppressed, whereby light usage efficiency can be improved.

The predetermined threshold described above is roughly a value that causes permissible reflection at the interface with the window and is at least smaller than the difference in refractive index between air and the light transmissive member.

It is preferable that the spectrometric apparatus according to the application example further includes a circuit substrate provided with a controller that controls the spectrometric apparatus, and the light blocking section contains carbon-based conductive fillers and hence has conductivity, and that the enclosure has a wiring line that achieves conduction between the light blocking section and the circuit substrate.

In the application example with this configuration, the light blocking section contains the carbon-based conductive fillers and therefore has conductivity. When conduction is achieved between the light blocking section and the circuit substrate via the connection wiring line, the light blocking section can be used as an electrode. For example, in a case where a subject under measurement is the outer layer of the skin, causing the light blocking section to come into contact with the outer layer of the skin allows the light blocking section to be used as a ground electrode that grounds the circuit substrate.

In the spectrometric apparatus according to the application example, it is preferable that the measurement module includes a light source section that irradiates a subject with light, a spectroscopic filter capable of selecting light of a predetermined wavelength from light from the subject and outputting the selected light and further capable of changing the wavelength of the light to be outputted, and a light reception section that receives the light from the spectroscopic filter.

In the application example with this configuration, a spectroscopic filter that separates the light from the light source is provided, and the spectroscopic filter is configured to be capable of changing the wavelength to be selected. The configuration readily allows spectrometry at a plurality of measurement wavelengths.

A storage case according to an application example of the invention is a storage case that accommodates a plurality of adhesive sheets each of which is formed of an adhesive member on which a peelable sheet is stuck, the adhesive member disposed on at least part of a surface of a spectrometric apparatus that acquires the amount of light having a wavelength under measurement contained in light incident on the spectrometric apparatus. The spectrometric apparatus includes a measurement module that acquires the amount of light and an enclosure that accommodates the measurement module and has a window that transmits light traveling toward the measurement module. An area which surrounds at least the window and in which the adhesive member is disposed is set on a surface of the enclosure, and the adhesive member has a light blocking section that is located in the area but in an area outside the window and surrounds the window in a plan view in a direction along an optical axis of the light traveling toward the measurement module and blocks light that belongs to a measurement wavelength region within which at least the wavelength under measurement is present. The storage case includes a bottom section having a placement surface on which the adhesive sheet is placed and a sidewall section that continuously extends from a peripheral portion of the placement surface and is provided along a direction in which the adhesive sheet approaches or separates from the bottom section. The sidewall section includes a first restricting section that comes into contact with at least part of an outer circumferential edge of the peelable sheet to restrict the position of the peelable sheet in a plane perpendicular to the approaching/separating direction and a second restricting section that comes into contact with at least part of an outer circumferential edge of the enclosure when the spectrometric apparatus is moved with the window facing the placement surface in the direction in which the spectrometric apparatus approaches or separates from the bottom section to restrict the position of the spectrometric apparatus in the plane perpendicular to the approaching/separating direction in such a way that the adhesive member overlaps with the area when viewed in the approaching/separating direction.

In the application example, the storage case, in which the first restricting section restricts the position of the peelable sheet in the plane perpendicular to the direction in which the peelable sheet approaches or separates from the bottom section (hereinafter also referred to as approaching/separating direction), allows the adhesive sheet to be placed in a predetermined position in the plane perpendicular to the approaching/separating direction. Thereafter, when the spectrometric apparatus is moved in the direction in which the spectrometric apparatus approaches or separates from the bottom section, the storage case, specifically, the second restricting section restricts the position of the spectrometric apparatus in the plane perpendicular to the approaching/separating direction so that the adhesive member coincides with an area where the adhesive member is disposed when viewed in the approaching/separating direction.

The configuration described above allows the adhesive member to be disposed in a predetermined position on the enclosure. That is, the light blocking section can be disposed in the predetermined position on the enclosure. A spectrometric apparatus capable of providing the advantageous effects of the application examples described above can therefore be reliably and readily configured.

BRIEF DESCRIPTION OF THE DRAWINGS

The invention will be described with reference to the accompanying drawings, wherein like numbers reference like elements.

FIG. 5A is a plan view of the adhesive sheet viewed in the thickness direction thereof, and FIG. 5B is a cross-sectional view showing a cross section of the adhesive sheet sectioned in the thickness direction.

DESCRIPTION OF EXEMPLARY EMBODIMENTS

An embodiment of the invention will be described below.

Figure 1:
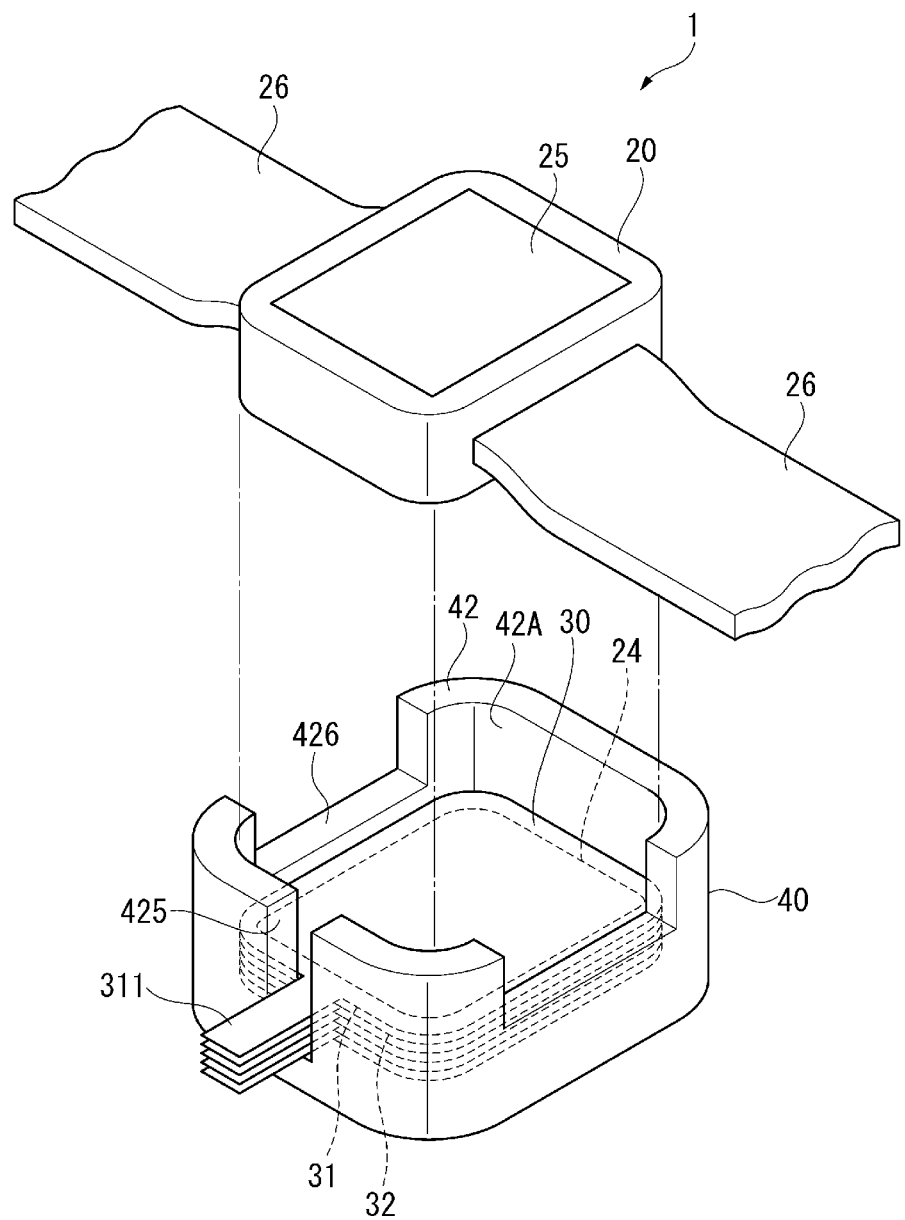
FIG. 1 is a perspective view showing schematic configurations of a biological body inspection apparatus and a storage case that stores an adhesive sheet including an adhesive member to be stuck on the biological body inspection apparatus according to an embodiment of the invention.

FIG. 1 is a perspective view showing a schematic configuration of a biological body inspection apparatus 1 as a spectrometric apparatus according to an embodiment of the invention and a schematic configuration of a storage case 40, which stores an adhesive sheet 30, which includes an adhesive member 24 to be stuck on the biological body inspection apparatus 1.

The biological body inspection apparatus 1 shown in FIG. 1 is caused to come into intimate contact with a subject under measurement, such as an arm of a person under measurement, irradiates the subject under measurement with light, acquires an optical spectrum of the light from the subject, and uses the optical spectrum to analyze components contained in the biological body. Although will be described later in detail, the adhesive member 24 is attached to the biological body inspection apparatus 1 in a predetermined position on a surface of a facing section that faces the subject under measurement at the time of measurement so that an enclosure 20 comes into intimate contact with the subject under measurement. The adhesive member 24 on which peelable sheets 31 and 32 are stuck is accommodated in the storage case 40 shown in FIG. 1. The storage case 40 can be used to attach the adhesive sheet 30 to the predetermined position on the surface of the facing section. The configurations of the adhesive sheet 30 and the storage case 40 will be described later in detail.

Configuration of Biological Body Inspection Apparatus

Figure 2:
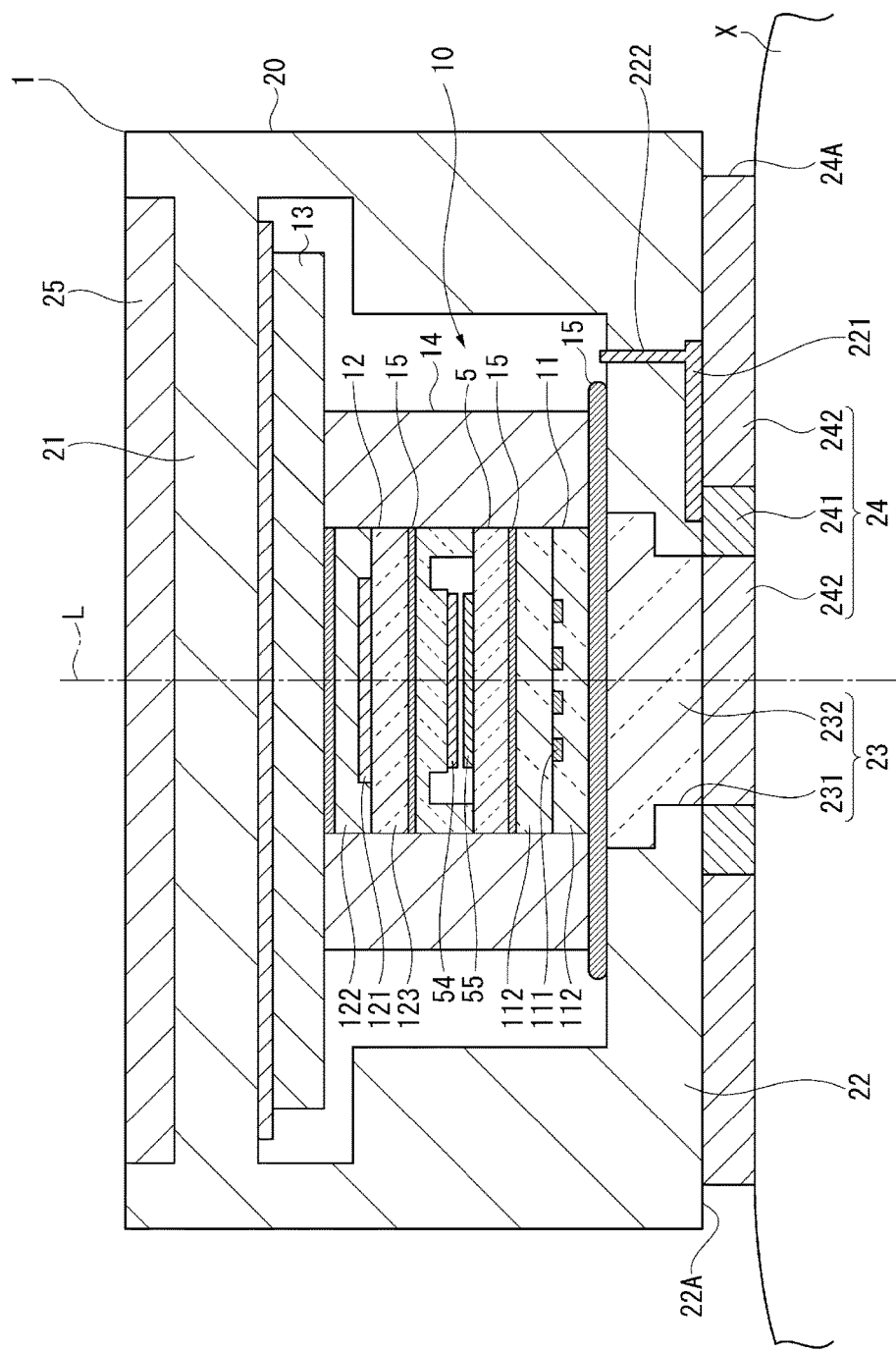
FIG. 2 is a cross-sectional view showing a schematic configuration of the biological body inspection apparatus.

FIG. 2 shows a schematic configuration of the biological body inspection apparatus 1.

The biological body inspection apparatus 1 according to the present embodiment corresponds to a spectrometric apparatus according to an embodiment of the invention and includes a measurement module 10 and the enclosure 20, which accommodates the measurement module 10, as shown in FIG. 2. The biological body inspection apparatus 1 exemplifies a configuration for measuring the degree of oxygen saturation in blood that flows through the biological body as an example.

Configuration of Measurement Module

The measurement module 10 includes a wavelength tunable interference filter 5, a light source section 11, a light reception section 12, and a circuit substrate 13, as shown in FIG. 2. The light source section 11, the wavelength tunable interference filter 5, and the light reception section 12 are covered with a tubular molded resin 14 and integrally fixed to the circuit substrate 13.

Configuration of Wavelength Tunable Interference Filter

Figure 3:
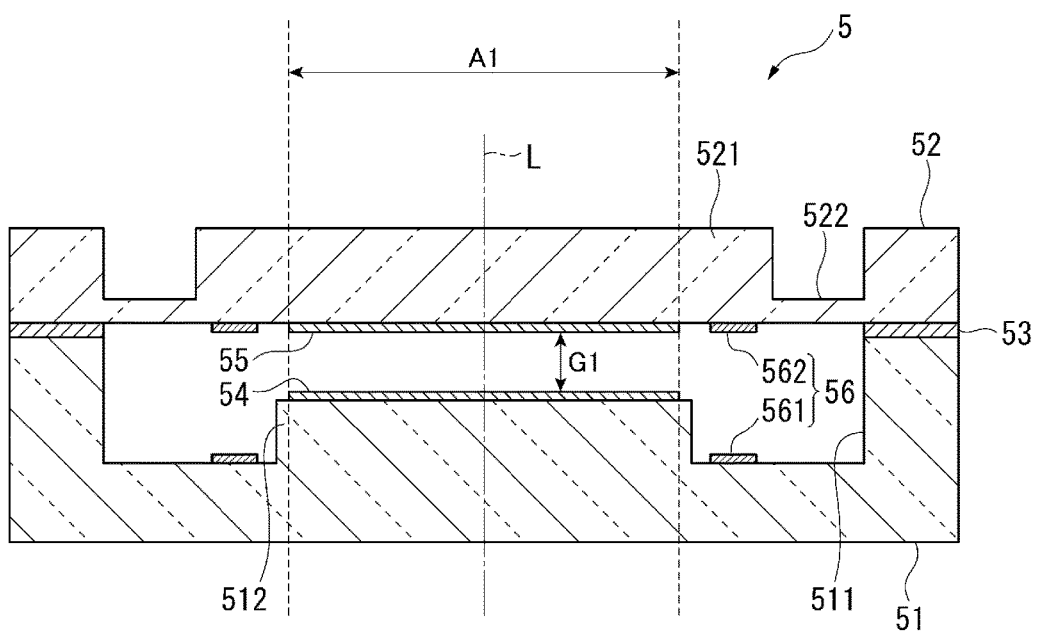
FIG. 3 is a cross-sectional view showing a schematic configuration of a wavelength tunable interference filter.

FIG. 3 is a cross-sectional view showing a schematic configuration of the wavelength tunable interference filter 5.

The wavelength tunable interference filter 5 is a spectroscopic device and transmits light of a predetermined wavelength out of light reflected off a subject under measurement. The wavelength tunable interference filter 5 includes alight transmissive fixed substrate 51 and a movable substrate 52, and the fixed substrate 51 and the movable substrate 52 are bonded to each other via a bonding film 53, which is formed, for example, of a plasma polymerization film primarily made, for example, of siloxane so that the fixed substrate 51 and the movable substrate 52 are integrated with each other. The thus configured wavelength tunable interference filter 5 has a smaller device size than, for example, in a case where an AOTF (acousto-optic tunable filter) or an LCTF (liquid crystal tunable filter) is used as the spectroscopic device, whereby the size of the measurement module 10 can be reduced.

The fixed substrate 51 has an electrode placement groove 511 and a reflection film attachment portion 512, which are formed in an etching process. A fixed electrode 561 is provided in the electrode placement groove 511, and a fixed reflection film 54 is provided on the reflection film attachment portion 512.

The fixed electrode 561 is so formed in the electrode placement groove 511 that the fixed electrode 561, for example, has an annular shape that surrounds the reflection film attachment portion 512.

The fixed reflection film 54 can be formed, for example, of a metal film made, for example, of Ag or an alloy film made, for example, of an Ag alloy. The fixed reflection film 54 may instead be formed of a dielectric multilayer film, for example, having a high refractive layer made of $TiO_2$ and a low refractive layer made of $SiO_2$. The fixed reflection film 54 may still instead be a reflection film formed of a metal film (or alloy film) layered on a dielectric multilayer film, a reflection film formed of a dielectric multilayer film layered on a metal film (or alloy film), or a reflection film that is a laminate of a single-layer refractive layer (made, for example, of $TiO_2$ or $SiO_2$) and a metal film (or alloy film).

The movable substrate 52 has a movable portion 521 and a holding portion 522, which is provided in an area outside the movable portion 521 and holds the movable portion 521, as shown in FIG. 3.

The movable portion 521 is formed to be thicker than the holding portion 522. In the present embodiment, for example, the movable portion 521 is formed to be as thick as the movable substrate 52. The movable portion 521 is so formed that it has a diameter greater than at least the diameter of the outer circumferential edge of the reflection film attachment portion 512 in a filter plan view. A movable electrode 562 and a movable reflection film 55 are provided on the movable portion 521.

The movable electrode 562 is so provided that it faces the fixed electrode 561. The movable reflection film 55 is disposed in a position where it faces the fixed reflection film 54 via a gap G1. The movable reflection film 55 is a reflection film having the same configuration as that of the fixed reflection film 54 described above. The wavelength tunable interference filter 5 extracts light according to the gap G1 from light under measurement that passes through an effective area A1, which faces the reflection films 54 and 55, and transmits the extracted light along an optical axis L, which is perpendicular to the reflection films 54 and 55.

The holding portion 522 is a diaphragm that surrounds the movable portion 521 and is formed to be thinner than the movable portion 521. The thus configured holding portion 522 is more readily bent than the movable portion 521 and can therefore displace the movable portion 521 toward the fixed substrate 51 under electrostatic attractive force having a small magnitude. The dimension of the gap G1 can therefore be changed with the fixed reflection film 54 and the movable reflection film 55 maintained parallel to each other.

In the present embodiment, the diaphragm-shaped holding portion 522 is presented by way of example, but the holding portion 522 is not necessarily formed of a diaphragm. For example, beam-shaped holding portions disposed at equal angular intervals may be provided around a plan-view center point.

In the thus configured wavelength tunable interference filter 5, the fixed electrode 561 and the movable electrode 562 form an electrostatic actuator 56, and the electrodes 561 and 562 are connected to a controller via a voltage control circuit (driver) that is not shown but is provided on the circuit substrate 13. When the voltage control circuit applies a voltage to the electrostatic actuator 56 under the control of the controller, electrostatic force according to the voltage acts between the electrodes 561 and 562, so that the dimension of the inter-reflection-film gap G1 is changed. The wavelength of the light that passes through the wavelength tunable interference filter 5 can thus be changed within a range of wavelengths under measurement.

Configurations of Light Source Section, Light Reception Section, and Circuit Substrate Referring back to FIG. 2, the light source section 11 irradiates a subject under measurement with light through a window 23, which is provided in the enclosure 20 and will be described later. The light with which the subject under measurement is irradiated only needs to be light used in component analysis, that is, light having an absorption wavelength (intrinsic wavelength) of a component under analysis. For example, the subject under measurement is irradiated with light within a visible light region to near infrared light region. The light source section 11 is formed of light sources 111, each of which is, for example, an LED, an OLED (organic light emitting diode), or a resistive heat generator, and which are provided in a light transmissive support substrate 112. The light sources 111 are disposed in positions where they do not interfere with the optical path of light traveling from a subject under measurement X toward the wavelength tunable interference filter 5 along the optical axis of the wavelength tunable interference filter 5, which will be described later. Further, a reflector or any other light guiding member that reflects the light from the light sources 111 toward the subject under measurement X, which is located on the side opposite the wavelength tunable interference filter 5, is disposed as appropriate on the side of the light sources 111 that faces the wavelength tunable interference filter 5.

The light reception section 12 receives light having passed through the wavelength tunable interference filter 5 and outputs a detection signal according to the amount of received light to the controller that is not shown. The light reception section 12 includes a light receiving device 121, a support substrate 122, in which the light receiving device 121 is provided, and a light transmissive substrate 123, which is disposed on the light receiving side of the light receiving device 121 (the side facing the wavelength tunable interference filter 5) and covers the light receiving device 121 and the support substrate 122. The light receiving device 121 can, for example, be an image sensor for image acquisition.

Although not shown, the circuit substrate 13 is provided with the controller (control section), which controls the biological body inspection apparatus 1. Further, the light source section 11, the wavelength tunable interference filter 5, and the light reception section 12, which are covered with the molded resin 14 as described above, are integrally fixed to the circuit substrate 13. The circuit substrate 13 is then fixed to the enclosure 20. It is noted that the light source section 11, the wavelength tunable interference filter 5, and the light reception section 12 are sequentially arranged. The space between the light source section 11 and the wavelength tunable interference filter 5 and the space between the wavelength tunable interference filter 5 and the light reception section 12 are each filled with a light transmissive resin 15, and these components are bonded to each other via the resin 15. Providing the resin 15 can therefore prevent reflection due to air layers that are otherwise formed between the light source section 11 and the wavelength tunable interference filter 5 and between the wavelength tunable interference filter 5 and the light reception section 12.

Configuration of Enclosure

The enclosure 20 has an accommodation space formed therein, and the accommodation space accommodates the measurement module 10, as shown in FIG. 2.

On the surface of the enclosure 20 are provided, a display section 25, operation buttons (not shown) that accept instructions from a user, and other components. The enclosure 20 is further provided with a belt-shaped band section 26 for attaching the biological body inspection apparatus 1 to an arm of the user or any other subject.

The enclosure 20 has several walls. One of two walls that intersect the optical axis L is a fixing section 21, to which the circuit substrate 13 is fixed, and the other wall is a facing section 22, which is aimed at the subject under measurement X at the time of measurement and faces the subject under measurement X.

The circuit substrate 13 is fixed to the inner surface of the fixing section 21, for example, with an adhesive.

The window 23, which guides light from the subject under measurement to the interior of the enclosure 20, is formed in a portion of the facing section 22 where the window 23 overlaps with the effective area A1. In the present embodiment, the space between the facing section 22 and the light source section 11 is also filled with the light transmissive resin 15, as shown in FIG. 2. Providing the resin 15 can prevent reflection due to an air layer that is otherwise formed between the facing section 22 and the light source section 11.

Figure 4:
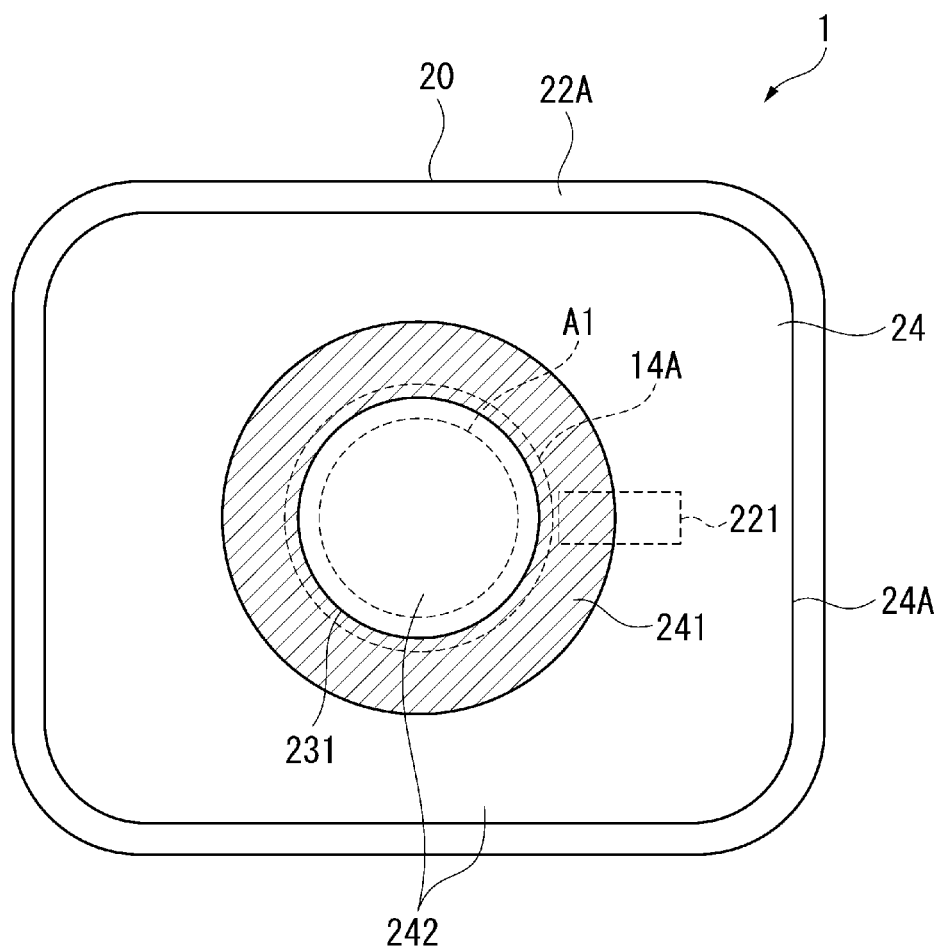
FIG. 4 is a plan view diagrammatically showing a surface of a facing section of the biological body inspection apparatus on which an adhesive member is stuck.

FIG. 4 shows a schematic configuration of the biological body inspection apparatus 1 viewed from the side where the facing section 22 is present.

The window 23 is so configured that a light transmissive member 232 is disposed in an opening 231 provided in the enclosure 20, as shown in FIGS. 2 and 4. The light transmissive member 232 is made of a material having light transmissivity, such as glass, quartz, polycarbonate and acryl.

In a plan view along the optical axis L, the opening 231 is preferably so formed that the dimension thereof is greater than the dimension of the effective area A1 but smaller than the dimension of an inner edge 14A of an open portion of the molded resin 14, as shown in FIG. 4. Setting the dimension of the opening 231 to be greater than the dimension of the effective area A1 allows light to be incident on the entire effective area A1. Further, setting the dimension of the opening to be smaller than the dimension of the inner edge 14A of the open portion of the molded resin 14 prevents part of the light incident through the opening from being reflected off an end surface that is a surface of the molded resin 14 and faces the facing section 22 and then forming stray light.

The adhesive member 24 is disposed on a surface 22A of the facing section 22. The adhesive member 24 is a sheet-shaped member so disposed that it covers the window 23 in the plan view along the optical axis L. The adhesive member 24 has a light blocking section 241, which is provided in an area outside the window 23 but inside an outer circumferential edge 24A of the adhesive member 24 and along the outer edge of the window 23 in the plan view described above so that the light blocking section 241 surrounds the window 23, and a light transmissive section 242, which is the section other than the light blocking section 241, as shown in FIG. 4. The adhesive member 24 is a member that is formed of the light blocking section 241 and the light transmissive section 242 integrated with each other and has adhesiveness.

The light blocking section 241 is made of a gel-like resin having adhesiveness and containing carbon-based conductive fillers. The carbon-based conductive fillers can be made of carbon black, carbon fibers, graphite, or any other carbon material having conductivity. The thus configured light blocking section 241 blocks light at least in the visible light region, which is a measurement wavelength region. The gel-like resin can be a silicone-based resin, an acrylic resin, an epoxy-based resin, a urethane-based resin, or any of other variety of resins.

The light blocking section 241 has conductivity and is in contact with a connection electrode 221, which is exposed through the surface 22A of the facing section 22. The connection electrode 221 is connected to the circuit substrate 13 via a connection wiring line 222 (partially not shown) and allows conduction between the circuit substrate 13 and the light blocking section 241. The light blocking section 241 is in contact with the subject under measurement, such as a human body, at the time of measurement and can therefore be grounded.

The light transmissive section 242 is provided in the portion other than the light blocking section 241 and is in intimate contact with the light transmissive member 232 in the portion where the light transmissive section 242 coincides with the window 23. The light transmissive section 242 is made of the gel-like resin having adhesiveness described above, and the difference in refractive index between the light transmissive section 242 and the light transmissive member 232 is smaller than or equal to a predetermined threshold. The predetermined threshold is roughly a value that causes permissible reflection at the interface between the light transmissive section 242 and the light transmissive member 232 and is at least smaller than the difference in refractive index between air and the light transmissive member 232.

The adhesiveness of the light blocking section 241, which contains the conductive fillers, lowers in some cases, and adjusting the size of the light transmissive section 242 as appropriate allows desired adhesive force to be achieved over the entire adhesive member 24.

The thus configured biological body inspection apparatus 1 is pressed against the subject under measurement X and performs spectrometry within a measurement wavelength region with the facing section 22 facing the subject under measurement X. That is, with the adhesive member 24 being in intimate contact with the surface of the subject under measurement X, the light source section 11 is caused to emit light, and the amount of light from the subject under measurement X is acquired at each measurement wavelength. The biological body inspection apparatus 1 acquires an optical spectrum from the acquired amount of light at each measurement wavelength and performs component analysis based on the acquired optical spectrum. The biological body inspection apparatus 1 can separate the optical spectrum into a plurality of spectral components having different peak positions and identify the type of a contained component and calculate the ratio among the contents of the contained components based on the spectral components. A component analysis method, a method for identifying each contained component, and a method for calculating the ratio among the contents of the contained components can be known methods.

Configuration of Adhesive Sheet

Figure 5A:
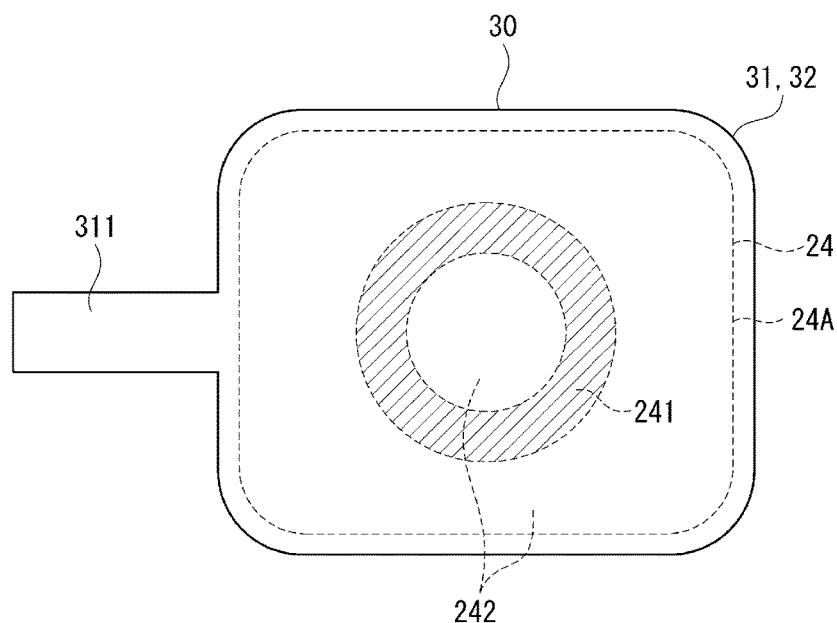
FIGS. 5A and 5B diagrammatically show the configuration of the adhesive sheet.
Figure 5B:
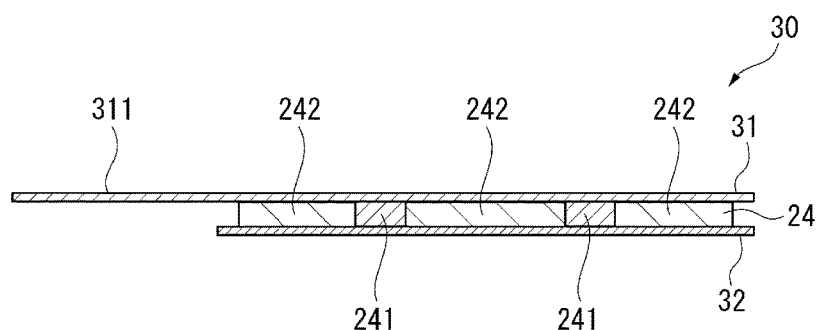

FIGS. 5A and 5B diagrammatically show the configuration of the adhesive sheet. FIG. 5A is a plan view of the adhesive sheet 30 viewed in the thickness direction, and FIG. 5B is a cross-sectional view showing a cross section of the adhesive sheet 30 sectioned in the thickness direction.

The adhesive sheet 30 includes the adhesive member 24 and a first peelable sheet 31 and a second peelable sheet 32, which are so disposed that they sandwich the adhesive member 24 in the thickness direction and allow the adhesive member 24 to be peeled off, as shown in FIG. 5B.

Each of the first peelable sheet 31 and the second peelable sheet 32 is, for example, a sheet formed of a substrate having a surface on which a resin or any other material is coated and allows the adhesive member 24 stuck on the surface to be readily peeled off.

In the plan view viewed in the thickness direction, each of the first peelable sheet 31 and the second peelable sheet 32 has a roughly rectangular external shape that roughly coincides with the external shape of the facing section 22 of the enclosure 20.

The first peelable sheet 31 has a protruding section 311, which protrudes outward from the first peelable sheet 31 from one side of the rectangular shape in the direction perpendicular to the one side, as shown in FIG. 5A. The protruding section 311 has a roughly rectangular external shape in the plan view in the thickness direction. Although will be described later, when the adhesive sheet 30 is accommodated in the storage case 40, the protruding section 311 is placed in a first groove 425 provided in the storage case 40.

Configuration of Storage Case

Figure 6:
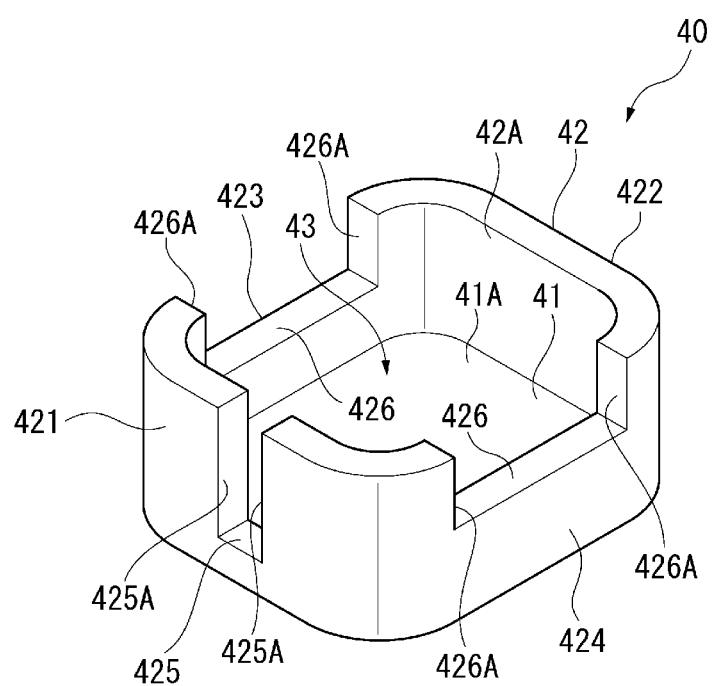
FIG. 6 is a perspective view showing a schematic configuration of the storage case.

FIG. 6 is a perspective view showing a schematic configuration of the storage case 40.

The storage case 40 shown in FIG. 6 accommodates a plurality of adhesive sheets 30 therein (see FIG. 1). Further, the storage case 40 is used as a fixture when the adhesive member 24 is stuck on a predetermined position on the biological body inspection apparatus 1.

The storage case 40 has a bottom section 41, which has a roughly rectangular shape, and a sidewall section 42, which stands from the outer circumferential edge of the bottom section 41 and surrounds the circumference of the bottom section 41, as shown in FIG. 6. A recess 43, which is formed by the bottom section 41 and the sidewall section 42, accommodates the adhesive sheets 30.

An inner surface 41A, which is a surface of the bottom section 41 and is surrounded by the sidewall section 42, functions as a placement surface on which the adhesive sheets 30 are placed. In a plan view in the thickness direction of the bottom section 41, an inner wall surface 42A of the sidewall section 42 is located in a position that roughly coincides with or is slightly shifted outward from the positions of an outer circumferential edge 20A of the enclosure 20 and an outer circumferential edge 30A of each of the adhesive sheets 30 (peelable sheets 31 and 32). The adhesive sheets 30 are therefore disposed on the inner surface 41A of the bottom section 41 with no warpage of the adhesive sheets 30.

The sidewall section 42 has a first sidewall portion 421, a second sidewall portion 422, which faces the first sidewall portion 421, a third sidewall portion 423, which is adjacent to the first sidewall portion 421, and a fourth sidewall portion 424, which faces the third sidewall portion 423.

Among the sidewall portions 421 to 424, the first sidewall portion 421 has the first groove 425. In the state in which the adhesive sheets 30 are accommodated in the storage case 40, the protruding section 311 of each of the first peelable sheets 31 is disposed in the first groove 425. The first groove 425 has a pair of first groove inner surfaces 425A, which are perpendicular to the bottom section 41 and face each other. The first groove 425 is so formed that the distance between the pair of first groove inner surfaces 425A, that is, the width of the first groove 425 is slightly greater than or roughly equal to the width of the protruding section 311 (dimension in the direction perpendicular to the protruding direction). Further, the first groove 425 is provided in part of a central portion of the sidewall portion 421 and reaches the bottom section 41 in the thickness direction described above.

Each of the third sidewall portion 423 and the fourth sidewall portion 424 has a second groove 426. The second groove 426 is provided in part of a central portion of each of the third sidewall portion 423 and the fourth sidewall portion 424 in the plan view described above.

In a state in which the biological body inspection apparatus 1 is disposed in the storage case 40, the band section 26 of the biological body inspection apparatus 1 is placed in the second grooves 426. Each of the second grooves 426 is so formed that the distance between a pair of second groove inner surfaces 426A, that is, the width of the second groove 426 is slightly greater than or roughly equal to the width of the band section 26 (dimension in the width direction of the belt-shaped band section 26).

The depth of each of the second grooves 426 is set at a dimension that prevents the groove bottom surface of the second groove 426 from interfering with the band section 26 in the state in which the biological body inspection apparatus 1 is disposed in the storage case 40.

The sidewall section 42 and the first groove 425 function as a first restricting section in an embodiment of the invention that comes into contact with at least part of the outer circumferential edge 30A of each of the adhesive sheets 30 (peelable sheets 31 and 32) to restrict the position of each of the adhesive sheets. The function of the first restricting section will be described later.

Similarly, the sidewall section 42 and the second grooves 426 function as a second restricting section in an embodiment of the invention that comes into contact with at least part of the outer circumferential edge 20A of the enclosure 20 to restrict the position of the enclosure 20. The function of the second restricting section will be described later.

Procedure of Sticking Adhesive Sheet

Figure 7:
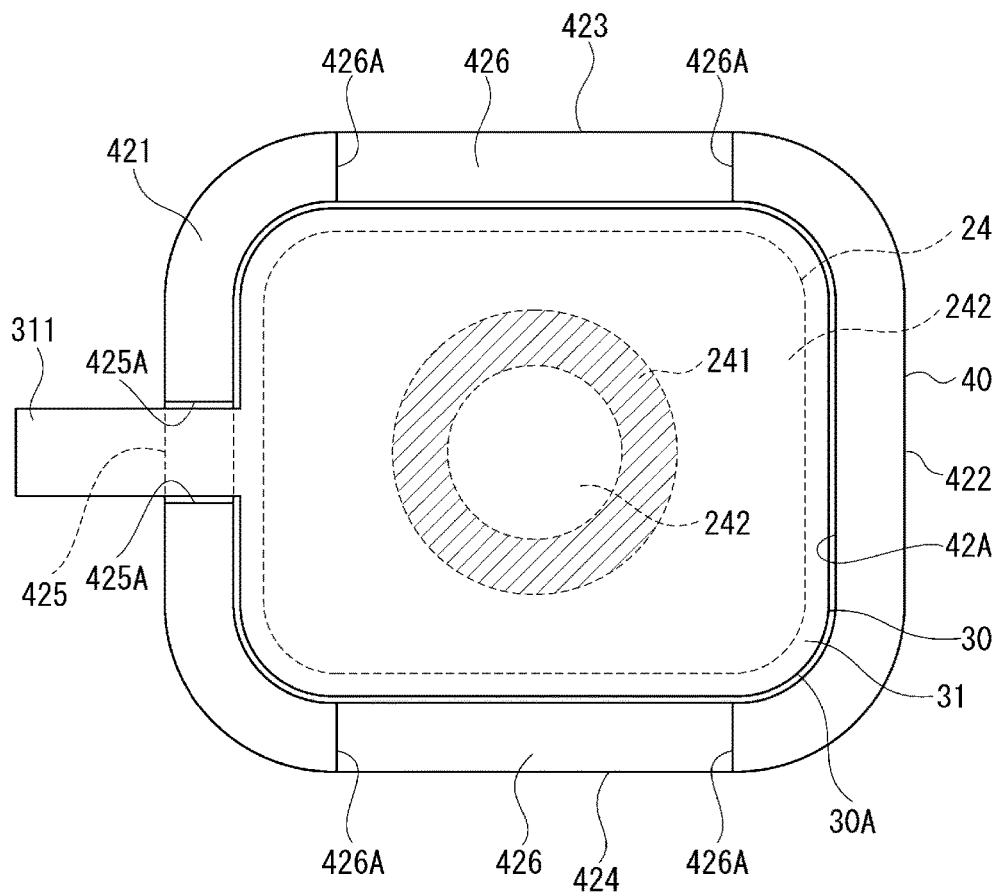
FIG. 7 shows the storage case which is placed on a horizontal surface and in which the adhesive sheet is accommodated in a top view in which the storage case is viewed from above in the vertical direction.
Figure 8:
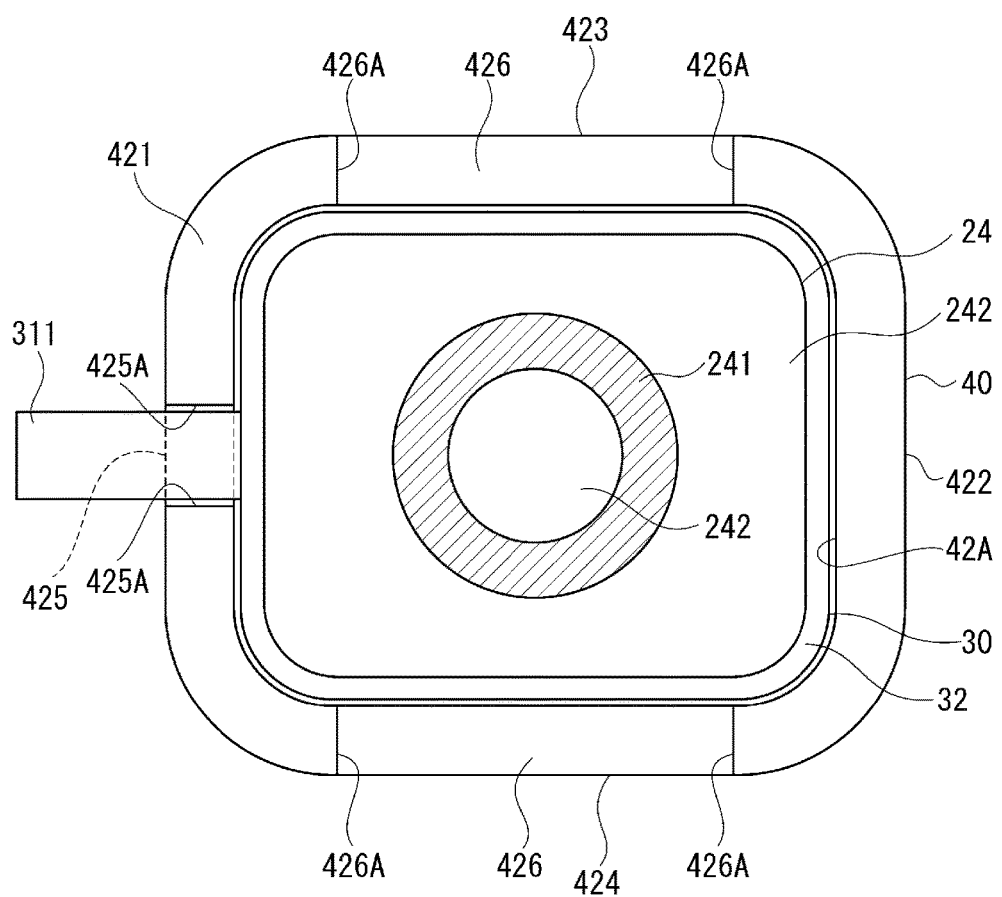
FIG. 8 shows the storage case which is placed on a horizontal surface and in which the adhesive sheet is accommodated in a top view in which the storage case is viewed from above in the vertical direction.
Figure 9:
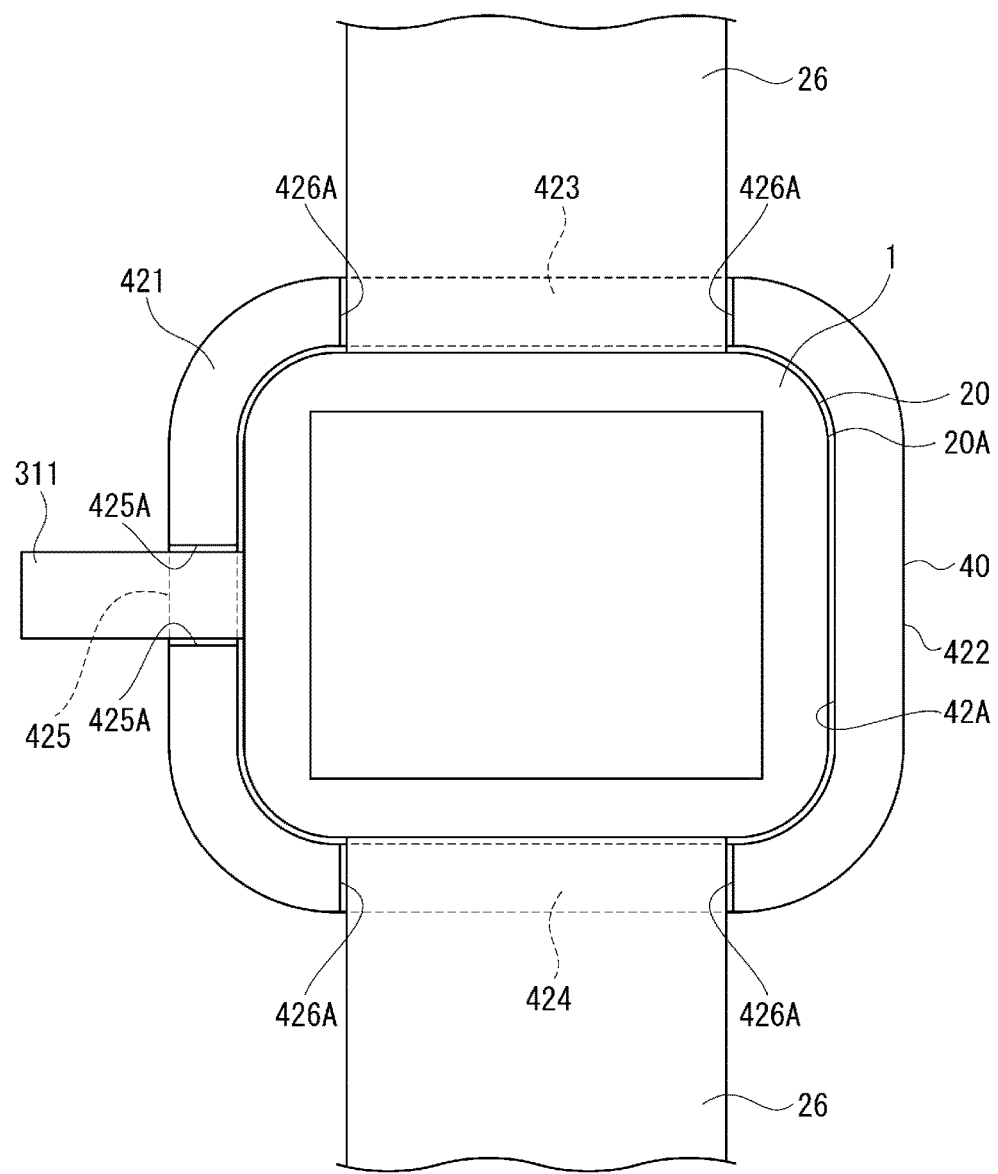
FIG. 9 shows the storage case placed on a horizontal surface with the biological body inspection apparatus placed in a recess of the storage case in a top view in which the storage case is viewed from above in the vertical direction.

FIGS. 7 to 9 are top views in which the storage case 40 so placed that the bottom section 41 is horizontally oriented is viewed in the vertical direction. In FIGS. 7 and 8, the storage case 40 accommodates the adhesive sheet 30. In FIG. 9, the biological body inspection apparatus 1 is placed in the storage case 40. In FIGS. 7 to 9, it is noted that the dimension of the gap between the inner wall surface 42A of the storage case 40 and the enclosure 20 of the biological body inspection apparatus 1/the adhesive sheet 30 is drawn to be greater than an actual dimension.

A plurality of (five in FIG. 1) adhesive sheets 30 are accommodated in the storage case 40 with the adhesive sheets 30 stacked in the vertical direction on the bottom section 41 of the storage case 40 (see FIG. 1). In this process, the adhesive sheets 30 are so accommodated in the storage case 40 that the outer circumferential edge of each of the peelable sheets 31 and 32 (outer circumferential edge 30A of each of adhesive sheets 30) follows the inner wall surface 42A of the storage case 40, as shown in FIG. 7. The adhesive sheets 30 are further so accommodated that the protruding section 311 of each of the first peelable sheets 31 passes through the first groove 425 and the outer edges of the protruding section 311 that extend along the protruding direction follow the first groove inner surfaces 425A. The adhesive sheets 30 can thus be disposed in a predetermined position in the storage case 40. Further, the user can readily take out or place each of the adhesive sheets 30 by using the protruding section 311.

Among the plurality of adhesive sheets 30, the first peelable sheet 31 on the uppermost adhesive sheet 30 is then peeled off (see FIG. 8). The adhesive sheet 30 located in the uppermost position is in a state in which the first peelable sheet 31 has been peeled off so that the adhesive member 24 is exposed, as shown in FIG. 8. Since the second peelable sheet 32 is so disposed that the outer circumferential edge thereof follows the inner wall surface 42A of the storage case 40, misalignment of the adhesive sheet 30 with the storage case 40 can be avoided when and after the first peelable sheet 31 is peeled off.

As shown in FIG. 9, the biological body inspection apparatus 1 with no adhesive member 24 on the facing section 22 (see FIG. 2) is moved downward in the vertical direction (direction in which facing section 22 approaches or separates from the bottom section 41) along the inner wall surface 42A of the storage case 40 with the facing section 22 oriented downward. The adhesive member 24 is then stuck on the facing section 22.

The enclosure 20 of the biological body inspection apparatus 1 is so formed that the outer circumferential edge 20A thereof viewed in the direction perpendicular to the facing section 22 is slightly smaller than the inner wall surface 42A of the storage case 40. The biological body inspection apparatus 1 is therefore moved in the vertical direction in a state in which at least part of the outer circumferential edge 20A comes into contact with the inner wall surface 42A and the position of the biological body inspection apparatus 1 in the horizontal plane, which is perpendicular to the approaching/separating direction, is restricted. A predetermined clearance (gap having a size of 0.6 mm, for example) is provided between the outer circumferential edge 20A of the enclosure 20 and the inner wall surface 42A so that the biological body inspection apparatus 1 accommodated in the storage case 40 is smoothly movable and the position of the biological body inspection apparatus 1 does not shift in a horizontal plane relative to the storage case 40. Therefore, since the biological body inspection apparatus 1 is moved along the inner wall surface 42A of the storage case 40, misalignment of the biological body inspection apparatus 1 in the storage case 40 can be avoided, and the adhesive member 24 can be stuck on the facing section 22 in a predetermined position.

Advantageous Effects of Embodiment

In the present embodiment, the adhesive member is disposed on the surface of the enclosure 20, specifically, in an area including the window 23 in the facing section 22. The adhesive member 24 has the light blocking section 241, which is located in an area outside the window 23 in the plan view in the direction along the optical axis L of the light received with the measurement module 10.

In the configuration described above, when the biological body inspection apparatus 1 is pressed against the subject under measurement X with the side where the window 23 is provided facing the subject under measurement X, the enclosure 20 is allowed to come into intimate contact with the subject under measurement X via the adhesive member 24. In this state, the light blocking section 241 of the adhesive member 24 that is in intimate contact with the subject under measurement X can block external light including light in a measurement wavelength region. Therefore, a situation in which external light having passed through a gap between the subject under measurement X and the enclosure 20 and further through the window 23 reaches the interior of the enclosure 20 and is received with the measurement module 10 can be avoided, whereby measurement accuracy can be improved.

Further, the adhesive member 24, which allows the enclosure 20 to come into intimate contact with the subject under measurement X, can prevent misalignment of the biological body inspection apparatus 1 with the subject under measurement X, whereby the measurement accuracy can be improved.

Further, in the present embodiment, the light transmissive section 242 is provided in an area outside the light blocking section 241. That is, the light blocking section 241 is provided in an area inside the outer circumferential edge 24A of the adhesive member 24. The adhesive member 24 tends to peel off in the vicinity of the outer circumferential edge 24A of the adhesive member 24. If the light blocking section 241 is provided along the outer circumferential edge 24A, there is a risk of entry of external light through a portion where the light blocking section 241 peels off. In contrast, in the present embodiment, in which the light blocking section 241 is provided in an area inside the outer circumferential edge 24A of the adhesive member 24, a situation in which the light blocking section 241 peels off can be avoided, whereby entry of external light can be more reliably avoided.

Further, in the present embodiment, the light transmissive section 242 is provided in regions inside and outside the light blocking section 241. The configuration, which allows the light transmissive section 242 provided in regions inside and outside the light blocking section 241 to come into intimate contact with a subject, can prevent the light blocking section 241 from peeling off. Therefore, entry of external light that occurs when the light blocking section 241 peels off can be more reliably avoided.

In the present embodiment, the light blocking section 241 contains the carbon-based conductive fillers, which provide a light blocking capability but lower adhesiveness in some cases. Even in such cases, causing the light transmissive section 242 provided in regions inside and outside the light blocking section 241 to come into intimate contact with the subject under measurement X can prevent the light blocking section 241 from peeling off, as described above.

Further, in the present embodiment, in the plan view along the optical axis L, the light blocking section 241 is provided along the outer edge of the opening 231 of the window 23. The configuration allows the light blocking section 241 to be provided in a position closer to the window 23. Therefore, even when the adhesive member 24 peels off in a position remote from the window 23, a situation in which the light blocking section 241 in the vicinity of the window 23 peels off can be avoided, whereby the entry of external light described above can be more effectively avoided.

Further, in the present embodiment, in which the adhesive member 24 is formed of the light blocking section 241 and the light transmissive section 242 integrated with each other, the adhesive member 24 can be exchanged through detachment and attachment thereof as a whole. Further, to place the adhesive member 24 in a predetermined area of the surface 22A of the facing section 22, the adhesive member 24 can be disposed as a whole. The light blocking section 241 can therefore be disposed in an appropriate position through alignment of the adhesive member 24 with the enclosure 20. The adhesive member 24 can thus be readily exchanged.

Further, the adhesive member 24 has the light transmissive section 242 that overlaps with the window 23 in the plan view along the optical axis L, and the light transmissive section 242 is disposed between the subject under measurement X and the window 23. The difference in refractive index between the light transmissive section 242 and the light transmissive member 232 is smaller than or equal to a predetermined threshold. In the configuration described above, the difference in refractive index at the interface with the light transmissive member 232 can be smaller than the difference in a case where an air layer is formed between the subject under measurement X and the window 23. Reflection at the interface can therefore be suppressed, whereby light usage efficiency can be improved.

Further, the light blocking section 241 contains the carbon-based conductive fillers and therefore has conductivity. When conduction is achieved between the light blocking section 241 and the circuit substrate 13 via the connection electrode 221 and the connection wiring line 222, the light blocking section 241 can be used as an electrode. For example, in a case where a subject under measurement is the outer layer of the skin, causing the light blocking section 241 to come into contact with the outer layer of the skin allows the light blocking section 241 to be used as a ground electrode that grounds the circuit substrate 13.

Further, in the present embodiment, the wavelength tunable interference filter 5 capable of changing the wavelength to be selected is provided as a spectroscopic filter that separates the light from the light source section 11. The configuration readily allows spectrometry at a plurality of measurement wavelengths.

Further, in the present embodiment, the storage case 40, in which the first groove 425, which serves as the first restricting section, and the inner wall surface 42A restrict the position of the first peelable sheet 31 and the second peelable sheet 32 in a plane perpendicular to the direction in which the peelable sheets approach or separate from the bottom section 41, allows the adhesive sheet 30 to be placed in a predetermined position in the plane perpendicular to the approaching/separating direction. Thereafter, when the biological body inspection apparatus 1 is moved in the approaching/separating direction, the storage case 40, specifically, the inner wall surface 42A, which serves as the second restricting section, restricts the position of the biological body inspection apparatus 1 in a plane perpendicular to the direction along the optical axis L (which coincides with the approaching/separating direction) so that the light blocking section 241 of the adhesive member 24 coincides with the portion of the surface of the enclosure 20 where the light blocking section 241 is disposed at the facing section 22, where the adhesive member 24 faces the enclosure 20, when viewed in the direction along the optical axis L (approaching/separating direction). The configuration described above allows the adhesive member 24 to be disposed in a predetermined position on the enclosure 20.

Variations of Embodiment

The invention is not limited to the embodiment described above and variations thereof, and variations, improvements, and other modifications to the extent that the advantage of some aspects of the invention is achieved fall within the scope of the invention.

In the embodiment described above, the configuration in which the adhesive member 24 is stuck on an entire preset intended area of the facing section 22 of the enclosure has been presented by way of example, but the invention is not necessarily configured this way. For example, in the plan view along the optical axis L, the light blocking section 241 only needs to be stuck on an area that is outside the window 23 and surrounds the entire circumference of the window 23. In the configuration described above, the light blocking section 241 may be stuck on a region shifted outward from the outer edge of the window 23 in the plan view described above.

Instead, the entire area of the adhesive member 24 outside the window 23 may form the light blocking section 241. Still instead, no light transmissive section 242 may be provided in the area inside the light blocking section 241 (area that overlaps with the window 23, for example) in the plan view described above. Still instead, an adhesive member 24 having no light transmissive section 242 provided not only in the area inside but also in the area outside the light blocking section 241 but having only the light blocking section 241 may be employed.

In the embodiment described above, the case where the wavelength under measurement is a wavelength within a visible light region has been described by way of example, but the invention is not necessarily configured this way, and the wavelength region under measurement may instead be a near infrared light region or any other wavelength region. In this case, the light blocking section 241 may be made of a material capable of blocking at least light of wavelengths that belong to the measurement wavelength region.

In the embodiment described above, the configuration in which the light blocking section 241 and the light transmissive section 242 of the adhesive member 24 are formed integrally with each other has been presented by way of example, but the invention is not necessarily configured this way, and the light blocking section 241 and the light transmissive section 242 may instead be provided as separate sections.

In the embodiment described above, the configuration in which the light blocking section 241 has conductivity has been presented by way of example, but the invention is not necessarily configured this way, and the light blocking section 241 may instead be so configured that it has no conductivity.

In the embodiment described above, in the plan view in the thickness direction of the bottom section 41, the outer circumferential edge of the enclosure 20 is shaped to be roughly the same as the inner wall surface 42A of the storage case 40 so that the enclosure 20 is moved along the inner wall surface 42A, but the invention is not necessarily configured this way, and a guide that positions the biological body inspection apparatus 1 relative to the storage case 40 and allows the biological body inspection apparatus 1 to move in the approaching/separating direction may be provided. Specifically, for example, a protrusion that extends along the direction in which the biological body inspection apparatus 1 approaches or separates from the bottom section 41 is formed on one of the inner wall surface 42A of the storage case 40 and the enclosure 20/adhesive sheet 30, a recess into which the protrusion is inserted is formed in the other, and the protrusion is inserted into the recess so that the biological body inspection apparatus 1 and the adhesive sheet 30 are positioned in a plane perpendicular to the approaching/separating direction. The recess and the protrusion may be formed of a plurality of recesses and protrusions.

In the embodiment described above, the configuration in which only one of the first peelable sheet 31 and the second peelable sheet 32 of the adhesive sheet 30, specifically, only the first peelable sheet 31 includes the protruding section 311 has been presented by way of example, but the invention is not necessarily configured this way, and the second peelable sheet 32 may also have a similar protruding section. The first groove 425 can therefore position the protruding section of the second peelable sheet 32, whereby the misalignment described above can be more reliably avoided. Further, when the biological body inspection apparatus 1 has the second peelable sheet 32 stuck thereon and the second peelable sheet 32 is peeled off the biological body inspection apparatus 1, using the protruding section of the second peelable sheet 32 allows the peeling off operation to be readily performed.

In the embodiment described above, the configuration in which the first groove 425 functions as the first restricting section, which restricts the position of the adhesive sheet 30, has been presented by way of example, but the invention is not necessarily configured this way, and the first groove 425 may instead be so configured that it has a width wider than the protruding section 311 and therefore does not have the function of the first restricting section.

In the embodiment described above, the configuration in which the second groove 426 functions as the second restricting section, which restricts the position of the band section 26, has been presented by way of example, but the invention is not necessarily configured this way, and the second groove 426 may be so configured that it has a width wider than the band section 26 and therefore does not have the function of the second restricting section.

In a case where no band section 26 is provided, the storage case 40 may be provided with no groove 426.

In the embodiment described above, the configuration in which the biological body inspection apparatus 1 includes the band section 26 has been presented by way of example, but the invention is not necessarily configured this way, and the biological body inspection apparatus 1 may include no band section 26.

In the embodiment described above, the configuration in which an output device as the display section 25 and an input device, such as operation buttons that are not shown, are provided has been presented by way of example, but the invention is not necessarily configured this way, and the input device or the output device described above may not be provided. In this configuration, the biological body inspection apparatus 1 may be configured to be capable of communicating with an external apparatus based on wired or wireless communication, and a variety of actions, such as measurement initiation and termination, may be controlled based on a control signal from the external apparatus. Further, the biological body inspection apparatus 1 may transmit a result of the measurement to the external apparatus.

In the embodiment described above, for example, the wavelength tunable interference filter 5 may be accommodated in a package that accommodates it alone, and the package may be incorporated in the measurement module 10. In this case, the package may be sealed and maintained under vacuum so that the electrostatic actuator 56 in the wavelength tunable interference filter 5 shows improved drive response to voltage application. When the wavelength tunable interference filter 5 is accommodated in such a package, the light source section 11 and the light reception section 12 may be disposed in the package, and no molded resin 14 may be provided.

In the embodiment described above, the wavelength tunable interference filter 5 includes the electrostatic actuator 56, which changes the dimension of the gap between the reflection films 54 and 55 through voltage application, but the wavelength tunable interference filter 5 is not necessarily configured this way.

For example, the wavelength tunable interference filter 5 may use an induction actuator having a first induction coil provided in place of the fixed electrode 561 and a second induction coil or a permanent magnet provided in place of the movable electrode 562.

Further, the electrostatic actuator 56 may be replaced with a piezoelectric actuator. In this case, for example, a lower electrode layer, a piezoelectric film, and an upper electrode layer are layered on each other and disposed at the holding portion 522, and a voltage applied between the lower electrode layer and the upper electrode layer can be changed as an input value to expand or contract the piezoelectric film so as to bend the holding portion 522.

In the embodiment described above, the wavelength tunable interference filter 5 is configured as a Fabry-Perot etalon and includes the fixed substrate 51 and the movable substrate 52 so bonded to each other that they face each other with the fixed reflection film 54 provided on the fixed substrate 51 and the movable reflection film 55 provided on the movable substrate 52, but the configuration of the wavelength tunable interference filter 5 is not limited thereto.

For example, the wavelength tunable interference filter 5 may instead be so configured that the fixed substrate 51 and the movable substrate 52 are not bonded to each other but a gap changer that changes the inter-reflection-film gap, such as a piezoelectric device, is provided between the substrates.

Further, the wavelength tunable interference filter 5 is not necessarily formed of two substrates. For example, a wavelength tunable interference filter having the following configuration may be used: Two reflection films are layered on a single substrate with a sacrifice layer between the reflection films; and the sacrifice layer is etched away or otherwise removed to form a gap.

In the embodiment described above, the wavelength tunable interference filter 5 has been presented as the spectroscopic filter by way of example, but the invention is not necessarily configured this way. For example, an AOTF (acousto optic tunable filter) or an LCTF (liquid crystal tunable filter) may be used as the spectroscopic device. From a viewpoint of size reduction of the apparatus, however, it is preferable to use a Fabry-Perot filter as in the embodiment described above.

In the embodiment described above, the biological body inspection apparatus has been presented as the spectrometric apparatus by way of example, but the invention is not necessarily configured this way. For example, the invention is applicable to a variety of apparatus that acquire a spectroscopic image and an optical spectrum, such as a spectroscopic camera that acquires a spectroscopic image and a component analyzer that performs component analysis on a food product as a subject under measurement.

In the embodiment described above, the configuration in which the measurement module including a spectroscopic filter capable of changing a wavelength under measurement is provided has been presented by way of example, but the invention is not necessarily configured this way. For example, a measurement module capable of performing spectrometry at a predetermined measurement wavelength may be employed.

In addition, the specific structure according to the embodiment of the invention can be an appropriate combination of the embodiment and the variations described above or changed as appropriate to any other structure in actual implementation of the invention to the extent that the advantage of the invention is achieved.

The entire disclosure of Japanese Patent Application No. 2014-221149 filed on Oct. 30, 2014 is expressly incorporated by reference herein.

What is claimed is:

1. A spectrometric apparatus comprising:
a measurement module that acquires an amount of measurement light having a measurement wavelength contained in light incident on the measurement module;
an enclosure that accommodates the measurement module and has a window that transmits the light traveling toward the measurement module; and
an adhesive member that is provided on a surface of the enclosure at least in a first area that surrounds the window,
wherein the adhesive member has a light blocking section that is located in a second area in the first area, the second area is located outside the window and surrounds the window in a plan view, and the light blocking section blocks the measurement light, and
the light blocking section further comprises a conductive ground electrode of the spectrometric apparatus.

2. The spectrometric apparatus according to claim 1, wherein the light blocking section is provided inside an outer circumferential edge of the adhesive member in the plan view.

3. The spectrometric apparatus according to claim 2, wherein the light blocking section is provided along an outer edge of the window in the plan view.

4. The spectrometric apparatus according to claim 1, wherein the adhesive member has a light transmissive section that transmits at least the measurement light, and the light blocking section and the light transmissive section are formed integrally with each other.

5. The spectrometric apparatus according to claim 1, wherein the adhesive member has a light transmissive section that is provided in a position where the light transmissive section overlaps with the window in the plan view and transmits at least the measurement light, the window has an opening provided in the enclosure and a light transmissive member disposed in the opening, and the light transmissive section has a refractive index that differs from a refractive index of the light transmissive member by an amount smaller than or equal to a predetermined threshold.

6. The spectrometric apparatus according to claim 1, further comprising a circuit substrate provided with a controller that controls the spectrometric apparatus, wherein the light blocking section contains carbon-based conductive fillers so that the light blocking section has conductivity, and the enclosure has a wiring electrically connecting between the light blocking section and the circuit substrate.

7. The spectrometric apparatus according to claim 1, wherein the measurement module further includes:
- a light source configured to irradiate a subject with light;
- a spectroscopic filter configured to select light of a predetermined wavelength from reflected light from the subject so as to transmit the selected light therethrough, and the spectroscopic filter is configured to change a wavelength of the light to be outputted; and
- a light reception sensor configured to receive the light from the spectroscopic filter.

* * * * *